US008530425B2

(12) United States Patent
Blumenfeld

(10) Patent No.: US 8,530,425 B2
(45) Date of Patent: *Sep. 10, 2013

(54) TARGETED DELIVERY OF BOTULINUM TOXIN TO THE SPHENOPALATINE GANGLION

(75) Inventor: Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 144 days.

This patent is subject to a terminal disclaimer.

(21) Appl. No.: 13/158,894

(22) Filed: Jun. 13, 2011

(65) Prior Publication Data

US 2012/0053127 A1 Mar. 1, 2012

Related U.S. Application Data

(63) Continuation of application No. 12/136,503, filed on Jun. 10, 2008, now Pat. No. 7,749,515, which is a continuation-in-part of application No. 11/296,079, filed on Dec. 7, 2005, now Pat. No. 7,655,244.

(60) Provisional application No. 60/593,641, filed on Feb. 1, 2005.

(51) Int. Cl.
*A61K 38/16* (2006.01)
*A61P 25/06* (2006.01)

(52) U.S. Cl.
USPC ......... 514/18.3; 424/239.1; 424/9.1; 530/350

(58) Field of Classification Search
USPC .................. 514/18.3; 424/236.1, 9.1, 239.1; 530/350
See application file for complete search history.

(56) References Cited

U.S. PATENT DOCUMENTS

| | | |
|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,139,845 A | 10/2000 | Donovan |
| 6,299,893 B1 | 10/2001 | Schwartz et al. |
| 6,306,423 B1 | 10/2001 | Donovan et al. |
| 6,312,708 B1 | 11/2001 | Donovan |
| 6,358,917 B1 | 3/2002 | Carruthers et al. |
| 6,423,319 B1 | 7/2002 | Brooks et al. |
| 6,447,787 B1 | 9/2002 | Gassner et al. |
| 6,458,365 B1 | 10/2002 | Aoki et al. |
| 6,464,986 B1 | 10/2002 | Aoki et al. |
| 6,623,742 B2 | 9/2003 | Voet |
| 6,838,434 B2 | 1/2005 | Voet |
| 7,172,763 B2 | 2/2007 | Aoki |
| 7,270,287 B2 | 9/2007 | First |
| 7,361,358 B2 | 4/2008 | Aoki et al. |
| 7,393,537 B2 | 7/2008 | Ackerman |
| 7,655,244 B2 | 2/2010 | Blumenfeld |
| 7,704,511 B2 | 4/2010 | Turkel |
| 7,749,515 B2 * | 7/2010 | Blumenfeld ............... 424/239.1 |
| 7,981,433 B2 * | 7/2011 | Blumenfeld ............... 424/239.1 |
| 2003/0224019 A1 | 12/2003 | O'Brien |
| 2004/0009180 A1 | 1/2004 | Donovan |
| 2005/0123567 A1 | 6/2005 | First |
| 2005/0191320 A1 | 9/2005 | Turkel et al. |
| 2005/0191321 A1 | 9/2005 | Turkel et al. |
| 2006/0104995 A1 | 5/2006 | Turkel et al. |
| 2008/0057084 A1 | 3/2008 | Burstein et al. |
| 2009/0252764 A1 | 10/2009 | Blumenfeld |

FOREIGN PATENT DOCUMENTS

| | | |
|---|---|---|
| DE | 101 50 415 A1 | 5/2003 |
| WO | WO 95/30431 | 11/1995 |
| WO | WO 03/011333 | 2/2003 |
| WO | WO 2004/078201 | 9/2004 |
| WO | WO 2006/083455 | 8/2006 |

OTHER PUBLICATIONS

Agur, A.M.R. and Dailey II, A.F., (2005) Atlas of Anatomy, 11th Ed., Lippincott Williams & Wilkins, Philadelphia, pp. 316, 317, 600, 601, 736.
Aoki K., et al, Mechanisms of the antinociceptive effect of subcutaneous Botox: Inhibition of peripheral and central nociceptive processing, Cephalalgia Sep. 2003;23(7):649.
Aoki K., Evidence for antinociceptive activity of Botulinum toxin type A in pain management. Headache 2003;43 Suppl 1:S9-15.
Aoki K., Pharmacology and immunology of Botulinum toxin serotypes. J Neurol 2001;248 Suppl 1:1/3-1/10.
Aoki, Current Medicinal Chemistry, 11:3085-3092, 2004.
Aoki, K.; et al., Botulinum toxin type A and other Botulinum toxin serotypes: a comparative review of biochemical and pharmacological actions, Eur J. Neurol 2001: (suppl 5); 21-29.
Aoki, K., Physiology and pharmacology of therapeutic Botulinum neurotoxins, in Kreyden, 0., editor, Hyperhydrosis and Botulinum toxin in dermatology, Basel, Karger; 2002; 30: pp. 107-116, at 109-110.
Bhattacharya K., et al., Novel uses of Botulinum toxin type A: two case reports, Mov Disord 2000; 15(Suppl 2):51-52.
Bigal ME, Sheftell FD, Rapoport AM, et al. Chronic daily headache in a tertiary care population: correlation between International Headache Society diagnostic criteria and proposed revisions of criteria for chronic daily headache. Cephalalgia 2002;22:432-438.
Bigalke H., et al., Botulinum A Neurotoxin Inhibits Non-Cholinergic Synaptic Transmission in Mouse Spinal Cord Neurons in Culture, Brain Research 360;318-324:1985.
Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244-251:1981.
Binder WJ, Brim MF, Blitzer A. Botulinum toxin type A (BOTOX) for treatment of migraine headaches: an open-label study. Otolaryngol Head Neck Surg 2000;123(6):669-676.

(Continued)

*Primary Examiner* — Chih-Min Kam
(74) *Attorney, Agent, or Firm* — Brigitte Phan; Ted Chan; Debra Condino

(57) ABSTRACT

*Botulinum* toxin, among other presynaptic neurotoxins is used for the treatment and prevention of migraine and other headaches associated with vascular disorders. Presynaptic neurotoxins are delivered focally, targeting the sphenopalatine ganglion. Exemplary delivery is carried out by way of injection.

18 Claims, 7 Drawing Sheets

(56) References Cited

OTHER PUBLICATIONS

Binz T. et al., The Complete Sequence of Botulinum Neurotoxin Type A and Comparison with Other Clostridial Neurotoxins, J Biological Chemistry 265(16);9153-9158:1990.
Blugerman G., et al., Multiple eccrine hidrocystomas: A new therapeutic option with Botulinum toxin, Dermatol Surg May 2003;29(5):557-559.
Blumenfeld AM, Dodick OW, Silberstein SD. Botulinum neurotoxin for the treatment of migraine and other primary headache disorders. Dermatol Clin 2004;22:167-175.
Blumenfeld AM. Botulinum toxin type A as an effective prophylactic treatment in primary headache disorders. Headache 2003;43:853-860.
BOTOX® (package insert). Irvine, California: Allergan Inc; 2004.
Brandes JL, Saper JR, Diamond M, et al. Topiramate for migraine prevention: a randomized controlled trial. JAMA;2004;291:965-973.
Brem, H.; et al, Placebo-Controlled Trial of Safety and Efficacy of Intraoperative Controlled Delivery by Biodegradable Polymers of Chemotherapy for Recurrent Gliomas, Lancet 345;1008-1012:1995.
Brin et al., Report of the Therapeutics and Technology Assessment Subcommittee of the American Academy of Neurology, Neurology, 40:1332-1336, 1990.
Brin MF, Fahn S, Moskowitz C, et al. Localized injections of Botulinum toxin for the treatment of focal dystonia and hemifacial spasm. Movement Dis 1 987;2:237-254.
Brin MF, Swope DM, O'Brien C, et al. BOTOX® for migraine: double-blind, placebo-controlled, region-specific evaluation. Cephalalgia 2000;20:421-422.
Brin, M., et al., Botulinum toxin type A: pharmacology, in Mayer N., editor, Spasticity: etiology, evaluation, management and the role of Botulinum toxin, 2002; pp. 110-124, at 112-113.
Bushara K., Botulinum toxin and rhinorrhea, Otolaryngol Head Neck Surg 1996:114(3):507.
Cao, Y., et al. Functional MRI of chronic daily headache. Cephalalgia 1999;19:462-463.
Castillo JP, Munoz P, Guitera V, et al. Epidemiology of chronic daily headache in the general population. Headache 1999;39:190-196.
Cheshire WP, Abashian SW, Mann JD. Botulinum toxin in the treatment of myofascial pain syndrome. Pain 1994;59:65-69.
Colas R, Munoz P, Temprano R, et al. Chronic daily headache with analgesic overuse: epidemiology and impact on quality of life. Neurology 2004;62:1338-1342.
Couch Jr. Placebo effect and clinical trials in migraine therapy. Meth Prob Migraine Trials, Neuroepid 1987:6:178-185.
Cui M, Khanijou S, Rubino J, et al. Subcutaneous administration of Botulinum toxin A reduces formalin-induced pain. Pain 2004;107:125-133.
Cui, M., et al., Mechanisms of the antinociceptive effect of subcutaneous BOTOX®: inhibition of peripheral and central nociceptive processing, Naunyn Schmiedebergs Arch Pharmacol 2002; 365 (supp 2): R17.
Dabrowski et al.; Botulinum toxin as a novel treatment for self mutilation in Lesch-Nyhan syndrome, Ann Neurol Sep. 2002;52(3 Supp 1):S157.
DasGupta et al., Biochemie, 71:1193-1200, 1989.
Depakote® ER (package insert). Abbott Laboratories; 2003.
Dowson, A.J., et al., Managing Chronic Headaches in the Clinic, Int J. Clin Pract., Dec. 2004, 58, 12,pp. 1142-1151.
Duggan et al.; A surbey of Botulinum neurotoxin substrate expression in cells; Mov Disord, 10(3):376: 1995.
Durham PL, Cady Ryan, Cady Roger. Regulation of calcitonin gene-related peptide secretion from trigeminal nerve cells by Botulinum toxin type A: implications for migraine therapy. Headache 2004;44:35-42.
European Agency for the Evaluation of Medicinal Products. Note for guidance on clinical investigation of medicinal products for the treatment of migraine. Dec. 2003.
Fedinic et al., Boll. 1st. Sieroter Milan, 64: 35-41, 1985.
Foster L, Clapp L, Erickson M, Jabbari B. Botulinum toxin A and chronic low back pain. A randomized, double-blind study. Neurol 2001 ;56:1290-1293.
Freund BJ, Schwartz M. Use of Botulinum toxin in chronic whiplash-associated disorder. Clin J Pain 2002;18(6 Suppl):S163-S168.
Fung L. K. et al., Pharmacokinetics of interstitial Delivery of Carmustine 4-Hydroperoxycyclophosphamide and Paclitaxel From a Biodegradable Polymer Implant in the Monkey Brain, Cancer Research 58;672-684: 1998.
Gawade et al., Brain Res., 334:139-146, 1985.
Gladstone JP., Gawel M. Newer formulations of the triptans: advances in migraine management, Drugs. 2003:63(21):2285-305.
Gladstone, J., et al., Chronic Daily Headache: A Rational Approach to a Challenging Problem, Seminars in Neurology, 2003, vol. 23, No. 3, pp. 265-275.
Goadsby et al., N. Eng. J. Med., 346:257-270, 2004.
Gonelle-Gispert et al.; snap-25a and -25b isoforms are both expressed in insulin-secreting cells and can function in insulin secretion;Biochem J 1;339 (pt 1):159-65:1999.
Guyton A.C. et al., Textbook of Medical Physiology, W.B. Saunders Company 1996, ninth edition; 686-688.
Habermann E., et al., Tetanus Toxin and Botulinum A and C Neurotoxins Inhibit Noradrenaline Release From Cultured Mouse Brain, J Neurochem 51(2);522-527:1988.
Habermann E., Inhibition by Tetanus and Botulinum A Toxin of the release of [3H]Noradrenaline and [3H]GABA From Rat Brain Homogenate, Experientia 44:224-226:1988.
Habermann, I-Labeled Neurotoxin from Clostridium Botulinum A: Preparation, Binding to Synaptosomes and Ascent to the Spinal Cord; Nauyn-Schmiedeberg's Arch. Pharmacol. 1974; 281, 47-56.
Harrison's Principles of Internal Medicine (1998), edited by Anthony Fauci et at., 14th edition, published by McGraw Hill.
Hershman et at., Infect. Immun., 62:421-425, 1994.
Headache Classification Committee of the International Headache Society. Classification and diagnostic criteria for headache disorders, cranial neuralgias and facial pain. Cephalalgia 1988;8 Suppl 7:1-96.
Headache Classification Subcommittee of the International Headache Society. The international classification of headache disorders, 2nd ed. Cephalalgia 2004;24 Suppl 1:1-151.
Heckmann M., et at., Botulinum toxin type a injection in the treatment of lichen simplex: An open pilot study, J Am Acad Dermatol Apr. 2002;46(4):617-9.
Hering R, Gardiner I, Catarci T, Witmarch T, Steiner T, de Belleroche J. Cellullar adaptation in migraineurs with chronic daily headache. Cephalalgia 1993;13:261-6.
Herold et al., Anesthesiology, 77:507-512, 1992.
Holroyd KA, Stensland M, Lipchik GL, et at. Psychosocial correlates arid impact of chronic tension-type headaches. Headache 2000; 40:3-16.
International Headache Society committee on Clinical Trials in Migraine. Guidelines controlled trials of drugs in migraine. First edition. Cephalalgia 1991; 11:1-12.
Jacks, L., et al., Idiopathic toe walking: Treatment with Botulinum toxin A injection, Dev Med Child Neurol 2002;44(Suppl 91):6).
Jahanshahi M., et al., Psychological functioning before and after treatment of torticollis with Botulinum toxin, J Neurol Neurosurg Psychiatry 1992; 55(3): 229-231.
Jankovic J. et al., Therapy With Botulinum Toxin, Marcel Dekker, Inc., (1994), pp. 5, 150.
Jost W., Ten years' experience with Botulinum toxin in anal fissure, Int J Colorectal Dis Sep. 2002;17(5):298-302.
Katsambas A., et al., Cutaneous diseases of the foot: Unapproved treatments, Clin Dermatol Nov.-Dec. 2002;20(6):689-699.
Klapper JA, Mathew NT, Klapper A et al. Botulinum toxin type A (BTX-A) for the prophylaxis of chronic daily headache. Cephalalgia 2000;20:292-293.
Li Y, et al., Sensory and motor denervation influences epidermal thickness in rat foot glabrous skin, Exp Neurol 1997;147:452-462 (see p. 459).
Linde M, Limmroth V, Dahlöf C, On behalf of the Headache Masters Programme. Ethical aspects of placebo in migraine research. Cephalalgia 2003;23:491-495.

Linton-Dahlöf, M Linde, Dahlöf C. Withdrawal therapy improves chronic daily headache associated with long-term misuse of headache medication: a retrospective study. Cephalalgia 2000;20:658-662.

Lipton RB, Bigal ME. Chronic daily headache: is analgesic overuse a cause or a consequence? Neurology 2003;61 :154-155.

Lipton RB, Stewart WF. Migraine headaches: epidemiology and comorbidity. Clin Neuroscience 1998:5:2-9.

Loder, E., et al., Use of Botulinum Toxins for Chronic Headaches: A Focused Review, The Clinical Journal of Pain, 2002, 18, pp. S169-S176.

Maizels, M., et al., The Patient with Daily Headaches, American Family Physician, Dec. 2004, vol. 70, No. 12, pp. 2299-2306.

Manzoni GC, Granella F, Sandrini G, et al. Classification of chronic daily headache by International Headache Society criteria: limits and new proposals. Cephalalgia 1995:15:37-43.

Marjama-Lyons, J., et al., Tremor-Predominant Parkinson's Disease, Drugs & Aging 16(4);273-278:2000.

Mathew N, Kaup A, Kailasam J. Botulinum toxin type A modifies chronic migraine further long-term (3years) experience with up to ten sets of treatments. Headache 2003:43:576.

Mathew NT, Reuveni U, Perez F. Transformed or evolutive migraine Headache 1987;27:102-106.

Mauskop A. Botulinum toxin in the treatment of chronic daily headaches. Cephalalgia 1999;19:453.

Schwartz BS, Stewart WF, Lipton RB. Loss of workdays and decreased work effectiveness associated with headache in the workplace. J Occup Environ Med 1997:39:320-327.

Sevim, S., et al., Botulinum toxin—A therapy for palmar and plantar Hyperhydrosis, Acta Neurol Belg Dec. 2002;102(4):167-170.

Shaari, et al., Otolaryngology—Head and Neck Surgery 112, 566-571 (1995).

Siegel S. Non-parametric statistics for the behavioral sciences. New York: McGraw-Hill Book Company, 1956:96:116-127.

Silberstein SD, Lipton RB, Sliwinski M. Classification of daily and near-daily headaches: field trial of revised IHS criteria. Neurology 1996:47:871-875.

Silberstein SD, Lipton RB, Solomon S, Mathew NT. Classification of daily and near-daily headaches: proposed revisions to the IHS criteria. Headache 1994;34:1-7.

Silberstein SD, Lipton RB. Chronic daily headache, including transformed migraine, chronic tension-type headache, and medication overuse. In: Silberstein SD, Lipton RB, Dalessio DJ, eds. Wolff's headache and other head pain, 7th ed. New York, NY: Oxford University Press;2001 :247-282.

Silberstein SD, Lipton RB. Chronic daily headache. Curr Opin Neurol 2000;13:277-283.

Silberstein SD, Neto W, Schmitt J, et al. Topiramate in migraine prevention. Arch Neurol 2004;61:490-495.

Silberstein SD, Silberstein MM. New concepts in the pathogenesis of headache. Part II. Pain Man 1990;3:334-342.

Silvestrini M, Bartolini M, Coccia M, et al. Topiramate in the treatment of chronic migraine. Cephalalgia 2003;23:820-824.

Simpson et al,. Pharmacol. Rev., 33:155-188, 1981.

Singh, Critical Aspects of Bacterial Protein Toxins, pp. 63-84 (chapter 4) of Natural Toxins II, edited by B.R. Singh et al., Plenum Press, New York (1996).

Sloop RR, Cole BA, Escutin RO. Reconstituted Botulinum toxin type A does not lose potency in humans if it is refrozen or refrigerated for 2 weeks before use. Neurology. Jan. 1997;48(1):249-53.

Smuts JA, Baker MK, Smuts HM, et al. Prophylactic treatment of chronic tension-type headache using Botulinum toxin type A. Eur J Neurol 1999;6(Suppl 4):599-5102.

Solomon GD, Sokbieranda FG, Genzen JR. Quality of life assessment among migraine patients treated with Sumatriptan. Headache 1995;35:449-454.

Spira PJ, Beran RG. Gabapentin in the prophylaxis of chronic daily headache: a randomized, placebo-controlled study. Neurology 2003;61 :1753-1759.

Stewart WF, Lipton RB, Celentano DD, et al. Prevalence of migraine headaches in the United States. Relation to age, income, race and other sociodemographic factors. JAMA 1992;267:64-69.

Suputtitada, A., Local Botulinum toxin type A injections in the treatment of spastic toes, Am J Phys Med Rehabil Oct. 2002;81(10):770-5.

Tepper and Dodick, Debate: Analgesic overuse is a cause, not a consequence, of chronic daily headache, Headache, 2002; 42:543-554.

Tepper, S., et al., Botulinum Toxin Type A in the Preventive Treatment of Refractory Headaches-Comparison Between Medication Overusers and Nonmedication Overusers Groups, Cephalalgia, 2003, 23, p. 715, poster P5N86.

Troost BT. Botulinum toxin type A (Botox) in the treatment of migraine and other headaches. Expert Rev Neurotherap 2004:4:27-31.

Wang SJ, Fuh JL, Lu SR. et al. Chronic daily headache in Chinese elderly: prevalence, risk factors and biannual follow-up. Neurology 2000;54:314-319.

Wang SJ, Fuh JL, Lu SR. et al. Quality of life differs among headache diagnoses: analysis of SF-36 survey in 901 headache patients. Pain 2001;89:285-292.

Weigand et al.; I-Labelled Botulinum A Neurotoxin: Pharmacokinetics in Cats after Intramuscular Injection; Naunyn-Schmiedeberg's Arch. Pharmacol. 1976; 292, 161-165.

Welch KM. Goadsby PJ. Chronic daily headache: nosology and pathophysiology. Curr Opin Neurol 2002:15:287-95. Review.

Wissel J, Muller J, Dressnandt J, Heinen F, Naumann M, Topka H, Poewe W. Management of spasticity associated pain with Botulinum toxin A. J Pain Symptom Manage 2000;20:44-9.

Woolf C. et al., Neuropathic Pain: Aetiology, Symptoms, Mechanisms, and Management, Lancet 1999; 353:1959-64.

Monzon MJ, Lainez MJA. Quality of life in migraine and chronic daily headache patients. Cephalalgia 1998;18:638-643.

Moyer E et al., Botulinum Toxin Type B: Experimental and Clinical Experience, being chapter 6, pp. 71-85 of "Therapy With Botulinum Toxin", edited by Jankovic, J. et al. (1994), Marcel Dekker, Inc.

Murry T., et al., Spasmodic dysphonia; emotional status and Botulinum toxin treatment, Arch Otolaryngol Mar. 1994; 120(3): 310-316.

Naumann et al; Botulinum toxin type A in the treatment of focal, axillary and palmar Hyperhydrosis and other hyperhidrotic conditions: European J. Neurology 6 (Supp 4): S111-S115:1999.

O'Brien PC, Fleming TR. A multiple testing procedure for clinical trials. Biometrics 1979:35:549-556.

Ondo WG, Vuong KD, Derman HS. Botulinum toxin A for chronic daily headache: a randomized, placebo-controlled, parallel design study. Cephalalgia 2004;24:60-5.

Payne M., et al, Botulinum toxin as a novel treatment for self mutilation in Lesch-Nyhan syndrome, Ann Neurol Sep. 2002;52(3 Supp 1):S157.

Pearce, L.B., Pharmacologic Characterization of Botulinum Toxin for Basic Science and Medicine, Toxicon 35(9);1373-1412 at 1393, (1997).

Purkiss J, Welch M, Doward S, et al. Capsaicin-stimulated release of substance P from cultured dorsal root ganglion neurons: involvement of two distinct mechanisms. Biochem Pharmacol 2000;59:1403-1406.

Rabasseda et al., Toxicon, 26:329-326, 1988.

Ragona et al.; Management of Parotid Sialocele With Botulinum Toxin; The Laryngoscope 109:1344-1346:1999.

Rahimtoola H, Buurma H, Tijssen CC, et al. Migraine prophylactic medication usage patterns in The Netherlands. Cephalalgia 2003;23:293-301.

Retie G, Granato A, Maria Antonello R, Zorzon M. Headache induced by chronic substance use: analysis of medication overused and minimum dose required to induce headache, Headache. Feb. 2004;44(2):148-153.

Rogers J., et al., Injections of Botulinum toxin A in foot dystonia, Neurology Apr. 1993;43(4 Suppl2).

Sanchez-Prieto, J., et al., Botulinum Toxin A Blocks Glutamate Exocytosis From Guinea Pig Cerebral Cortical Synaptosomes, Eur J. Biochem 165:675-681:1987.

Saper JR, Lake AE III, Cantrell DT, et al. Chronic daily headache prophylaxis with tizanidine: a double-blind, placebo-controlled, multicenter outcome study. Headache 2002;42:470-482.

Schantz, E.J., et al, Properties and use of Botulinum toxin and Other Microbial Neurotoxins in Medicine, Microbial Rev. 56;80-99:1992.

Scher AI, Stewart WF, Liberman J, et al. Prevalence of frequent headache in a population sample. Headache 1998;38:497-506.

Schim, J, et al., Effect of Preventive Treatment with Botulinum Toxin Type A on Acute Headache Medication Usage in Migraine Patients, Current Medical Research Opinions, vol. 20, No. 1, 2004, pp. 49-53.

* cited by examiner

HEADACHE PAIN PATHWAYS

TARGETED DELIVERY OF BOTULINUM TOXIN TO THE SPHENOPALATINE GANGLION

CROSS REFERENCE TO RELATED APPLICATIONS

This application is a continuation of application Ser. No. 12/136,503, filed Jun. 10, 2008, now U.S. Pat. No. 7,749,515, which is a continuation-in-part of application Ser. No. 11/296,079, filed Dec. 7, 2005, now U.S. Pat. No. 7,655,244, which claims the benefit of and priority to U.S. Provisional Application No. 60/593,641, filed Feb. 1, 2005, now abandoned, the entire contents of each are herein incorporated by reference in their entireties.

FIELD OF THE INVENTION

The present invention generally relates to the use of *botulinum* toxin to treat pain, rhinorrhea or excessive lacrimation by targeting ganglion, such as the sphenopalatine ganglion, for example.

BACKGROUND OF THE INVENTION

Migraine is a primary headache disorder that may be characterized by unilateral throbbing pain which worsens with head movement. This can be associated with other symptoms including nausea, light and noise sensitivity, lacrimation, nasal congestion, and rhinorrhea. An array of factors can trigger migraine headache, such as internal changes (hormonal changes, stress, sleep deprivation) or external changes (weather changes, alcohol, flickering light).

In some cases, a migraine attack begins with a premonitory visual aura. These patients experience a visual disturbance in the form of a zigzag spectrum around a blind spot, which grows in size over a 20-30 min period. This visual effect is known as the "fortification spectrum." The development of the fortification spectrum over time has been shown to correspond to a wave of depression in the activity of cortical neurons, which typically begins in the occipital lobe, and spreads anteriorly. The establishment of this correspondence has permitted the elaboration of a theory about the pathophysiological changes that may cause migraine and other headaches.

As neurons depress, they release nitric oxide (NO), which triggers the dilation of meningeal blood vessels. This vasodilation can result in a dull headache, which corresponds to the earliest phase of migraine.

The dilation of the meningeal blood vessels increases the activity of the nerve endings of the primary afferent neurons of the trigeminal nerve that are wrapped around them. As a result, the trigeminal cells release calcitonin gene related protein (CGRP), a vasodilator neuropeptide which further increases the dilation of the meningeal blood vessels, and further feeds into the trigeminal nerve activation. The local intracranial increased activation of the trigeminal nerve spreads through the trigeminal ganglion into the Trigeminal Nucleus Caudalis (TNC) in the brainstem in a process known as peripheral sensitization. The activation of the TNC leads in turn to a central activation process, through its thalamic and cortical projections, which are illustrated in FIG. 1.

Although the pain associated with migraine involves input from meningeal arteries, activation of the TNC may result in referred pain anywhere along the trigeminal network, including the temporal arteries and temporal muscles. The trigeminocervical network involved in the pathophysiology of migraine contains the three main branches of the trigeminal nerve: the ophthalmic branch (V1), the maxillary branch (V2), and the mandibular branch (V3), as illustrated in FIG. 2; as well as the sensory nerves for the posterior head and neck (C2, C3, C4, C5) that feed into the TNC. A detailed anatomical map of the relevant pathways can be found in pages 316, 317, 600, 601 and 736 of Agur, A. M. R. and Dalley II, A. F. (2005) Atlas of Anatomy 11$^{th}$ Ed., Lippincott Williams & Wilkins, Philadelphia, which is hereby incorporated by reference.

The activation of the TNC in the brainstem can further spread to the occipital nerve by virtue of its anatomical connection to the TNC, leading to pain sensation in the occipital area.

The activation of the TNC can also spread to the parasympathetic system, by activation of a nearby nucleus in the brainstem, the Superior Salivatory Nucleus (SSN), which is connected to the nucleus caudalis through a network of interneurons, as shown in FIG. 3.

Neurons from the SSN synapse with the Sphenopalatine ganglion, which provides vasomotor innervation to blood vessels and secretomotor innervation to the lacrimal glands, nasal and sinus mucosa. When the parasympathetic system is activated, the upper respiratory tract symptoms associated with migraine occur including, potentially, nasal symptoms (rhinorrhea, and post nasal drip), ocular symptoms (conjunctival injection, and tearing) and sinus congestion (pain or pressure around the sinuses). Other parasympathetic projections further aggravate the cascade of events, like the Sphenopalatine ganglion afferents that innervate the meningeal blood vessels. Activation of the parasympathetic system during a migraine attack is also accompanied by a significant increase in the levels of Vasoactive Intestinal Polypeptide (VIP), a parasympathetic neurotransmitter which causes vasodilation and can be measured in high concentrations during a migraine in the jugular venous drainage.

The increased activity of the trigeminal, occipital and parasympathetic systems just described is common to the so-called Trigeminal Autonomic Cephalgias (TAC), which include Cluster headache, Paroxysmal Hemicrania, SUNCT Syndrome, and Hemicrania Continua. Cluster headaches are a primary headache disorder involving attacks of less than 3 hours of duration with severe unilateral peri-orbital and temporal pain. These headaches can be associated with lacrimation, nasal congestion, rhinorrhea, conjunctival injection and a Horner's syndrome. The attacks occur in distinct clusters. Cluster headaches typically involve a series of disabling attacks on a daily basis lasting for months at a time. This pattern recurs annually or biannually.

Paroxysmal hemicrania is a primary headache disorder involving frequent attacks of unilateral, peri-orbital and temporal pain typically lasting less than 30 minutes. The pain can be associated with conjunctival injection, lacrimation, nasal congestion, rhinorrhea, ptosis and eyelid edema.

SUNCT Syndrome is a primary headache disorder characterized by multiple attacks of unilateral, peri-orbital and temporal pain typically lasting less than 2 minutes. The pain is associated with conjunctival injection, lacrimation, nasal congestion, rhinorrhea, and eyelid edema. This headache may be associated with trigeminal neuralgia.

Hemicrania Continua is a primary headache disorder characterized by a strictly unilateral headache responsive to Indomethacin. The pain is associated with conjunctival injection, lacrimation, nasal congestion, rhinorrhea, ptosis, and eyelid edema.

The trigeminal nerve is involved in the pain sensations for all of these headache types, as well as headaches triggered by other pathologies. For example, Temporal Arteritis involves inflammation of the temporal artery with painful palpable nodules along the artery. In addition to headache in the temporal area, Temporal Arteritis causes vision loss and jaw pain.

Headaches can also be associated with ischemic stroke. In a stroke, a lack of blood supply to brain tissue causes a sudden localized neurological deficit. In a large number of affected patients, occlusion of the arteries is due to the presence of atherosclerotic plaques in the arteries supplying the brain, for example, the carotid artery and the vertebral basilar artery. The atherosclerotic plaques are often associated with inflammation which further contributes to occlusion of the blood vessel.

Nociceptive fibers stimulated by inflammatory mediators in infectious or allergic rhinitis can also activate the trigeminal brainstem nucleus and precipitate migraine.

TAC and migraine are difficult to treat. Numerous medications have been used to prevent cluster and migraine headaches from occurring, which include, amongst others: propranolol, timolol, divalproex sodium, topiramate, verapamil, indomethacin and amitriptyline. These medicines have numerous side effects and patients are poorly compliant with them. In the case of TAC, indomethacin, in particular, is difficult for patients to tolerate due to gastro-intestinal upset.

All of the headache disorders described above produce disability and better treatment modalities are needed.

Additionally, rhinorrhea (postnasal drip) and excessive lacrimation are disorders in need of effective treatments. The patency of the nasal pathway is regulated by the autonomic nervous system. Sympathetic activity decreases nasal airway resistance by constricting nasal capacitance vessels and venous sinusoids, and parasympathetic activity produces nasal mucus from submucosal seromucinous glands. Nasal mucus is composed of 96 percent water and about 3 percent mucin. Excessive parasympathetic activity produces a copious flow of clear watery secretions. Therapeutic efforts to decrease rhinorrhea in human have attempted to either sever the parasympathetic nerve supply through Vidian neurectomy or chemically block the mucosal receptors for acetylcholine using short-acting, topical atropine analogs.

Recently, *Botulinum* toxin has been shown to be effective to treat migraine headaches when injected in the face, cranium and neck (Binder, U.S. Pat. No. 5,714,468). *Botulinum* toxin is a potent polypeptide neurotoxin produced by the gram positive bacterium *Clostridium botulinum* which causes a paralytic illness in humans termed botulism. *Botulinum* toxin has a light and a heavy chain. The heavy chain attaches to a cell surface receptor and the complex is then endocytosed. After endocytosis, the light chain translocates from the endosome into the cytoplasm, where it cleaves a segment of the SNARE protein complex responsible for vesicle fusion in the presynaptic nerve terminal. As a result, the release of neurotransmitters from these vesicles is effectively blocked for 3-6 months.

There are 7 immunologically distinct toxins: A, B, C1, D, E, F and G (Simpson, et al., Pharmacol. Rev., 33:155-188, 1981). These toxins bind to presynaptic membranes of target nerves and appear to work in a similar fashion (Brin, et al., "Report of the Therapeutics and Technology Assessment Subcommittee of the American Academy of Neurology", Neurology, 40:1332-1336, 1990). *Botulinum* toxin shows a high affinity for cholinergic neurons. *Botulinum* toxin type A produces a reversible, flaccid paralysis of mammalian skeletal muscle, presumably by blocking the exocytosis of acetylcholine at peripheral, presynaptic cholinergic receptors (Rabasseda, et al., Toxicon, 26:329-326, 1988). However, flaccid muscular paralysis is not necessary to achieve the reduction or prevention of migraine symptomatology. In fact, headache pain reduction may be observed at dosages of presynaptic neurotoxin which are lower or higher than dosages required to produce flaccid paralysis of skeletal muscle and without introduction of the neurotoxin into muscle tissue (Binder, U.S. Pat. No. 5,714,468).

Although the molecular basis for the sensation of migraine pain is not clear (Goadsby, et al., N. Eng. J. Med., 346:257-270, 2004), *Botulinum* toxin might exert its analgesic effect by blocking the release of nociceptive and inflammatory agents that are released during migraine, and not by blocking the release of acetylcholine. Because *Botulinum* toxin does not act on acetylcholine directly, but on the SNARE protein complex that mediates vesicle fusion, the release of other molecules which is also mediated by the SNARE protein complex is also affected by the toxin (Aoki, Current Medicinal Chemistry, 11:3085-3092, 2004). In fact, studies have shown that *Botulinum* toxin can also block the release of substance P, which is associated with neurogenic inflammation and pain generation (Aoki, Current Medicinal Chemistry, 11:3085-3092, 2004), glutamate, also associated with nociception (Cui, et al., Pain, 107:125-133, 2004), epinephrine, norepinephrine, and calcitonin gene-related peptide (Aoki, Current Medicinal Chemistry, 11:3085-3092, 2004). *Botulinum* toxin type A does not appear to cause degeneration of nervous or muscular tissue and has been approved for use in certain therapies by the U.S. Food and Drug Administration.

In addition to *Botulinum* toxin type A, other presynaptic neurotoxins have also been suggested to be useful for the treatment of migraine, given the functional characteristics they share with *Botulinum* toxin (Binder, U.S. Pat. No. 5,714, 468). One of these presynaptic neurotoxins is *Tetanus* neurotoxin, which is produced by *Clostridium tetani* (DasGupta, et al., Biochemie, 71:1193-1200, 1989), and shows significant sequence homology with serotypes A and E of *Botulinum* toxin. In particular, fragment Ibc of the *Tetanus* toxin, which is obtained by peptide digestion of the toxin, appears to act peripherally to produce flaccid paralysis (Fedinic, et al., Boll.1st. Sieroter Milan, 64: 35-41, 1985; and, Gawade, et al., Brain Res., 334:139-46, 1985).

Staphylococcal alpha-toxin has also been suggested for therapeutic use. This toxin stimulates the production in the brain of muscle-relaxing factor (MRF), which results in reversible, flaccid paralysis of skeletal muscle (Harshman, et al., Infect. Immun., 62:421-425, 1994). Staphylococcal alpha-toxin may function similarly to *Botulinum* toxin.

Other toxins which cause reversible, flaccid paralysis are the acylpolyamine toxins, which are anticholinergic, presynaptic neurotoxins produced in the venom of many invertebrates (Herold, et al., Anesthesiology, 77:507-512, 1992). For example, toxins AR636 and AG489 from spiders *Argiope aurantia* and *Agelenopsis aperta* lead to motor inhibition at a dosage of 2 micrograms and sensory inhibition at 7 micrograms.

Since the use of presynaptic neurotoxins to treat migraines was initially implemented by administering the toxins in the face, cranium and/or neck (Binder, U.S. Pat. No. 5,714,468), the hypothesis about the physiological changes underlying migraine has been significantly developed. The present invention provides an improvement in the therapeutic and preventive use of *Botulinum* toxin, among other presynaptic neurotoxins, to treat migraines, TAC and other headaches associated with vascular conditions by using a new method to administer these neurotoxins. The improvement is based on the recent theory that has emerged about the pathophysiological changes triggering these headaches, which involves the trigeminal, occipital and parasympathetic systems and therefore affects the administration sites of the toxins.

SUMMARY OF THE INVENTION

There is a need in the medical field to provide an effective therapeutic and prophylactic treatment for migraines, TAC, and other headaches associated with vascular conditions. The present invention provides a method for reducing or preventing symptoms and in particular pain related to migraines, TAC, and other headaches associated with vascular conditions in mammals, particularly humans. Specifically, the invention provides an improvement for current methods to treat and prevent these headaches with presynaptic neurotoxins. More specifically, the present invention relates to administering a therapeutically effective amount of a pharmaceutically safe presynaptic neurotoxin, to the sphenopalatine ganglion of a mammal.

The presynaptic neurotoxins of the invention will be those presynaptic neurotoxins that produce reversible, localized paralysis of musculature when administered to a mammal (although to practice the invention such paralysis is not needed) and do not cause degeneration of muscle or nervous tissue. *Botulinum* toxin, and in particular, *Botulinum* toxin type A is a preferred presynaptic neurotoxin of the invention.

In one embodiment, a method for reduction of headache pain in a mammal is provided comprising: administering by injection to the sphenopalatine ganglion, in a pharmaceutically safe form to a mammal, a therapeutically effective amount of a presynaptic neurotoxin. In one embodiment the presynaptic neurotoxin is a *botulinum* toxin including, but not limited to *botulinum* toxin types A, B, C, D, E, F and G. In another embodiment, the presynaptic neurotoxin is *Botulinum* toxin type A.

In another embodiment, the headache pain is associated with a headache from the group consisting of migraine, trigeminal autonomic cephalgia and headache caused by a vascular condition.

In yet another embodiment of the methods, the administering step comprises the steps of identifying an injection site midway between the tragus of the ear and the outer cantus of the eye; inserting a syringe at an angle of about 50-70 degrees relative to the vertical plane of the face; stopping the forward motion of the syringe upon reaching the maxillary bone; injecting the presynaptic neurotoxin at the sphenopalatine ganglion; and withdrawing the syringe.

In one embodiment, the administering step is performed bilaterally. In another embodiment, the administering step is performed unilaterally.

In another embodiment, the presynaptic neurotoxin is injected a discrete manner at a plurality of locations adjacent to the sphenopalatine ganglion.

In one embodiment disclosed herein, a method for reduction of headache pain in a mammal is provided comprising: administering by injection to the sphenopalatine ganglion, in a pharmaceutically safe form to a mammal, a therapeutically effective amount of *Botulinum* toxin type A.

In another embodiment, a method for reduction of rhinorrhea in a mammal is provided comprising administering by injection to a sphenopalatine ganglion, in a pharmaceutically safe form to a mammal, a therapeutically effective amount of *botulinum* toxin, selected from the group consisting of *botulinum* toxin types A, B, C, D, E, F and G. "*Botulinum* toxin" means a *botulinum* neurotoxin as either pure toxin or complex, and excludes *botulinum* toxins which are not neurotoxins such as the cytotoxic *botulinum* toxins $C_2$ and $C_3$.

In another embodiment, a method for reduction of lacrimation in a mammal is provided comprising administering by injection to a sphenopalatine ganglion, in a pharmaceutically safe form to a mammal, a therapeutically effective amount of *Botulinum* toxin type A.

BRIEF DESCRIPTION OF THE DRAWINGS

FIG. 4 has been adapted from Agur, A. M. R. and Dalley II, A. F. (2005) Atlas of Anatomy 11.sup.th Ed., Lippincott Williams & Wilkins, Philadelphia. Refer to pages 316, 317, 600, 601 and 736 of the original reference for a detailed view of the anatomy.

DETAILED DESCRIPTION OF THE INVENTION

Figure 1:
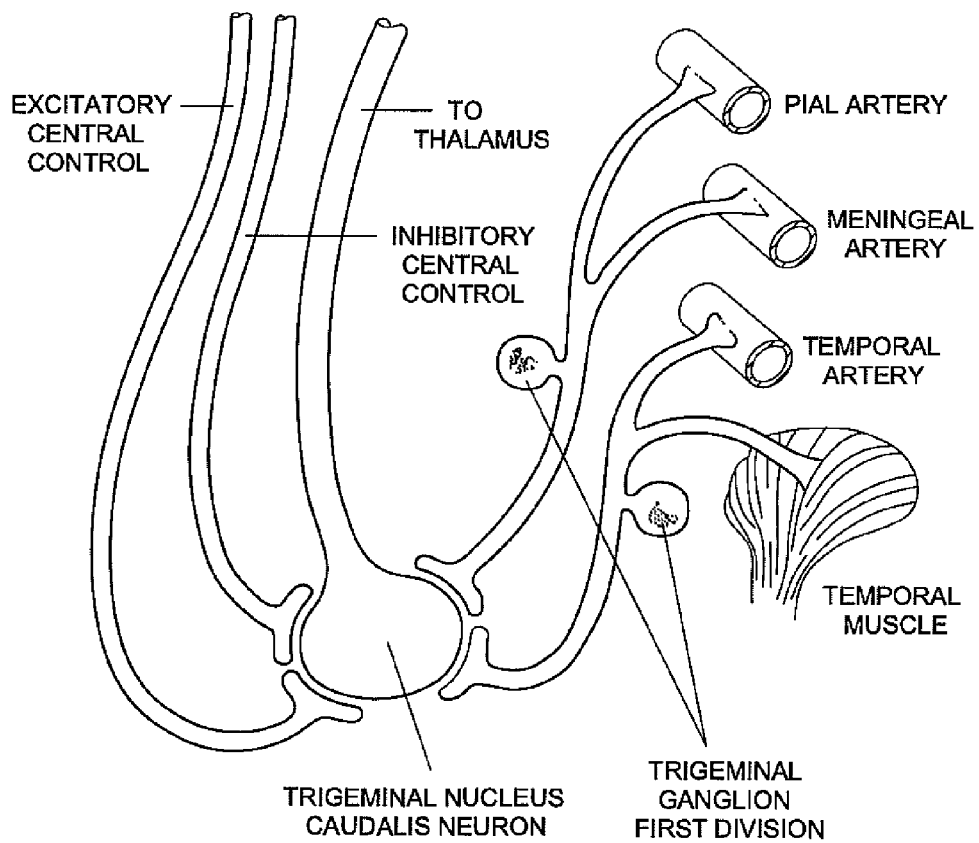
FIG. 1 depicts headache pain pathways, illustrating the input and output pathways of the trigeminal nucleus caudalis in the brainstem.
Figure 2:
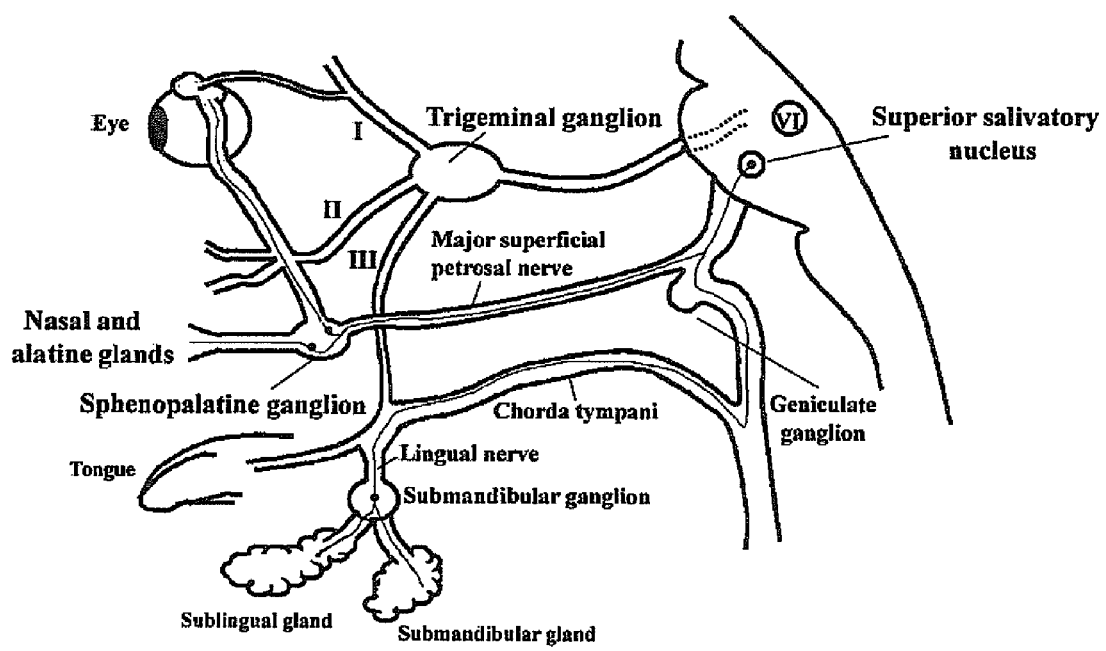
FIG. 2 depicts the trigeminal and parasympathetic network involved in headache pain, from and into the brainstem.
Figure 3:
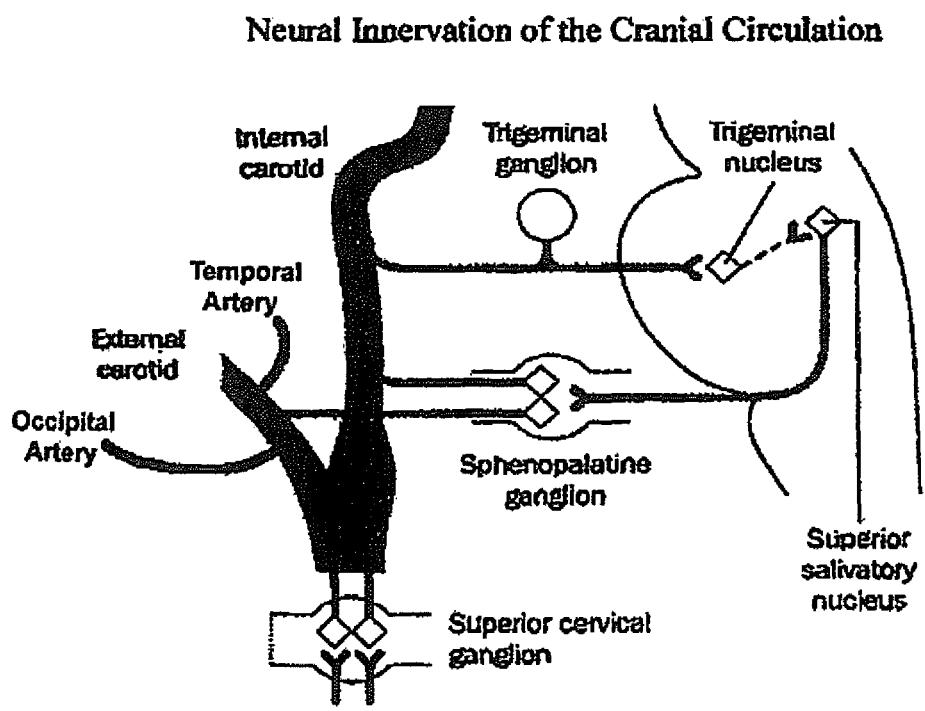
FIG. 3 depicts the neural innervation of the cranial circulation, illustrating the trigeminal nociceptive input from the internal carotid to the trigeminal nucleus caudalis of the brainstem, and the connection to the parasympathetic system through the superior salivatory nucleus. The parasympathetic system feeds back into the internal and external carotids, which connect with the temporal and occipital arteries.
Figure 4:
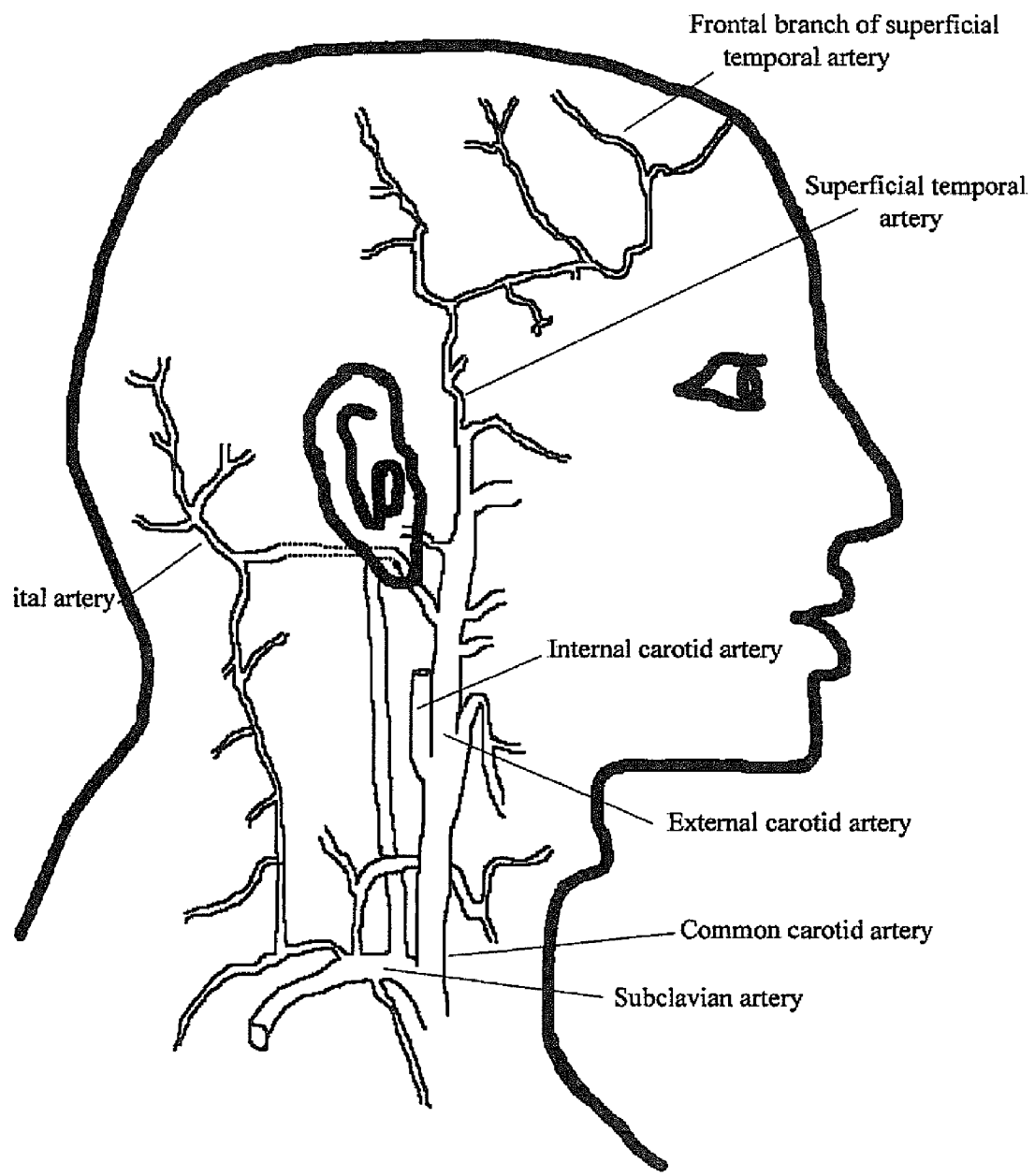
FIG. 4 depicts an illustrated lateral view of a human head showing the connection between the external carotid and the superficial temporal and occipital arteries.
Figure 5:
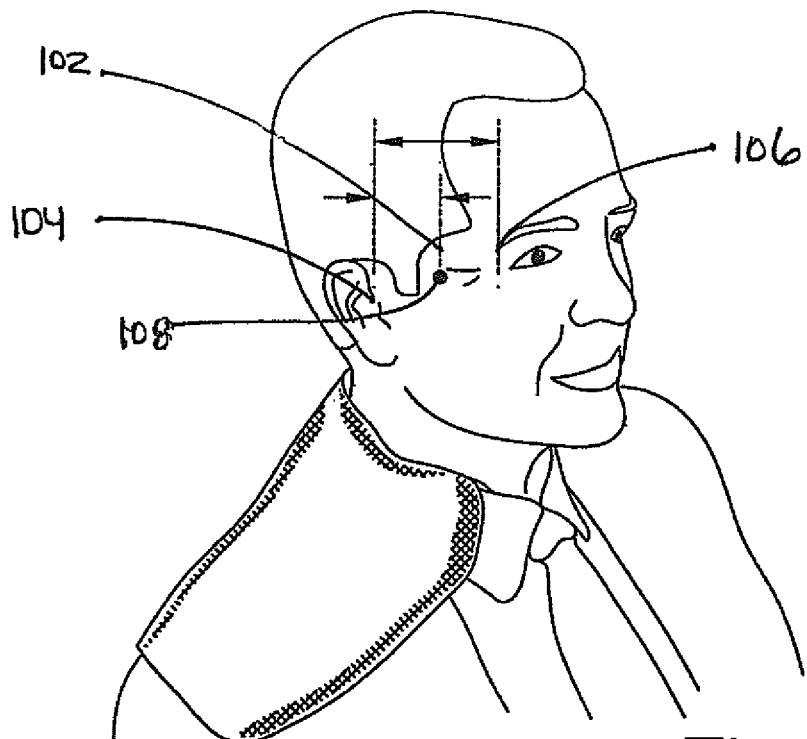
FIG. 5 depicts mapping of the anterior temporal fossa.
Figure 6:
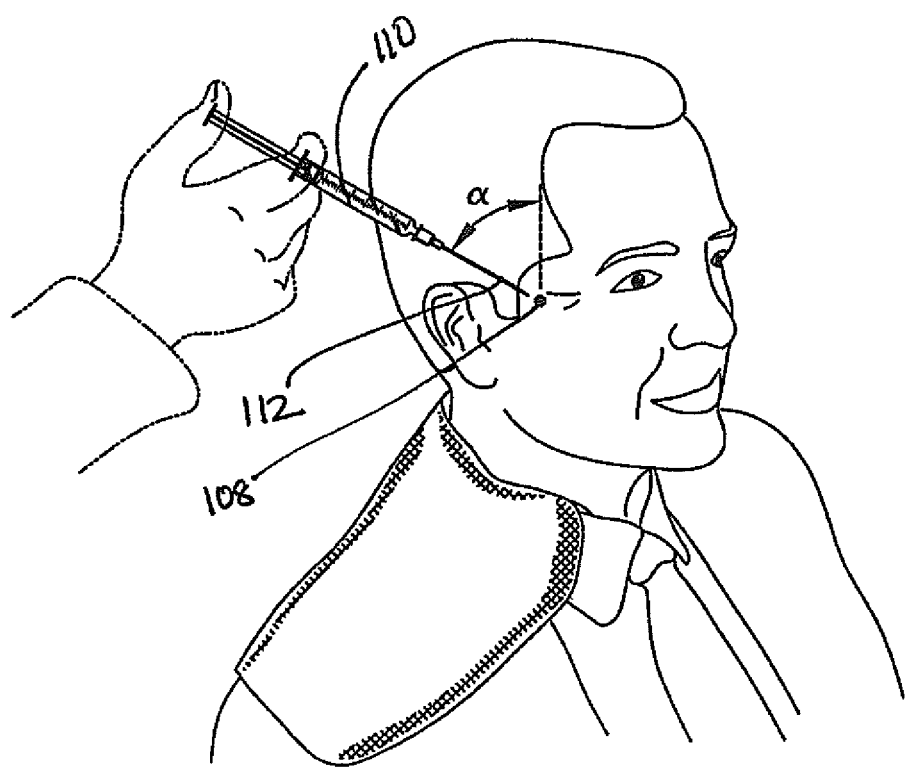
FIG. 6 depicts injection of a postsynaptic neurotoxin by insertion of a needle at angle $\alpha$.

The anatomical and physiological theory of migraine, trigeminal autonomic cephalgias (TAC), and other headaches associated with vascular conditions, as described in the Background section, suggests that blockade of the release of nociceptive and inflammatory agents triggered by the hyperactivation of the trigeminal, occipital and parasympathetic systems involved in the development of these headaches should provide an effective therapeutic and/or prophylactic treatment. As depicted in FIGS. 1 and 2, some of the anatomical pathways involved in the development of these headaches are intracranial; therefore, specific blockade of the intracranial pathways involved by non-invasive means is not feasible. However, some of the pathways affected are located extracranially under the surface of the skin or intranasally, and are therefore accessible to treatment. Some examples of these pathways include the temporal arteries and muscles (FIGS. 1 and 4), the nasal glands and mucosa (FIG. 2) and the occipital nerve and artery (FIG. 4). The current disclosure relates to providing a method for blocking the release of nociceptive and inflammatory agents triggered by the hyperactivation of the trigeminal, occipital and parasympathetic fibers that is increased during migraine, TAC or other headaches associated with vascular conditions.

Furthermore, the current disclosure provides methods for treating rhinorrhea or excessive lacrimation by injection of a presynaptic neurotoxin to the sphenopalatine ganglion.

The therapeutic modality used to treat and/or prevent the conditions described in this disclosure is the use of presynaptic neurotoxins. "Presynaptic neurotoxin" as used herein refers to those neurotoxins and their derivatives which are known to produce localized, reversible flaccid paralysis of musculature in mammals which does not result in degeneration of muscle or nervous tissue. However, as stated earlier, flaccid muscular paralysis which the disclosed presynaptic neurotoxins will produce is not necessary to achieve the reduction or prevention of headache symptomatology with the disclosed methods.

In one embodiment, the presynaptic neurotoxin of the invention is *Botulinum* toxin. In one useful embodiment of the invention, the presynaptic neurotoxin is *Botulinum* toxin type A. *Botulinum* toxin type A is presently supplied and commercially available as "BOTOX®" by Allergan, Inc. of Irvine, Calif., and as "Dysport®" by Ipsen, of Berkshire, UK. In another embodiment of the invention, the presynaptic neurotoxin is *Botulinum* toxin B. *Botulinum* toxin B is commercialized as "Neurobloc®"/"Myobloc®" by Solstice Neuroscience, Inc, of San Francisco, Calif. A pentavalent toxoid of all eight known *Botulinum* serotypes is also available as an investigational drug from the U.S. Center for Disease Control in Atlanta, Ga. The *Botulinum* A toxin preparations are most preferred for their known safety and efficacy. BOTOX® has also been used to treat, among other things, cervical dystonia, brow furrows, blepharospasm, strabismus, and hyperhidrosis.

*Tetanus* toxins are also commercially available for use as vaccines. Since the Ibc fragment of the *Tetanus* toxin is likely to act in a similar fashion to *Botulinum* toxin, as suggested earlier, a further embodiment of the present methods will comprise the use of pharmaceutically safe forms of the Ibc fragment of the *Tetanus* toxin rather than the intact form of the toxin.

Obtaining the presynaptic neurotoxins, including the *Botulinum* and *Tetanus* toxins, in a pharmaceutically safe form and therapeutically effective amount should be known or easily determined by those of ordinary skill in the art. The presynaptic neurotoxins should preferably be in a nonteratogenic form that does not trigger a detectable immune response. Pharmaceutical safety will be dose-dependent for most of the presynaptic neurotoxins, in such a way that fairly low doses of toxin will be "safe" as compared to doses known to produce disease.

The presynaptic neurotoxins will be preferably administered as a composition in a pharmaceutically suitable carrier. For this purpose, presynaptic neurotoxin compositions will be prepared for administration by combining a toxin of the desired degree of purity with physiologically suitable sterile carriers. These carriers will not produce toxic responses in recipients at the doses and concentrations used. In a preferred embodiment, the preparation of such compositions typically involves mixing the presynaptic neurotoxin with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. These compositions can also be lyophilized and will be pharmaceutically acceptable; i.e., appropriately prepared and approved for use in the desired application.

To facilitate administration, the presynaptic neurotoxins can be formulated in unit dosage form. The presynaptic neurotoxins may be supplied, for example, as a sterile solution or as a lyophilized powder in a vial.

In general, the amount of presynaptic neurotoxins used for treatment will be determined by the age, gender, presenting condition and weight of the patient, in consideration of the potency of the presynaptic neurotoxin. The potency of a toxin is expressed as a multiple of the $LD_{50}$ value for a reference mammal. One "unit" of toxin is the amount of toxin that kills 50% of a group of mammals that were disease-free prior to inoculation with the toxin. For example, one unit of *Botulinum* toxin is defined as the $LD_{50}$ upon intraperitoneal injection into female Swiss Webster mice weighing 18-20 grams each. One nanogram of the commercially available *Botulinum* toxin type A typically contains about 40 mouse units. The potency in humans of the *Botulinum* toxin type A product currently supplied by Allergan, Inc. as "BOTOX®" is estimated to be about $LD_{50}=2,730$ units.

Assuming an approximate potency of $LD_{50}=2,730$ units, the presynaptic neurotoxin can be administered in a dose of up to about 1,000 units; however, dosages of as low as about 2.5 to 5 units will have therapeutic efficacy. Dosages between 2.5 or 5 units and as high as 250 units will be normally used, and in one embodiment, individual dosages will be of about 15-30 units. Typically, the presynaptic neurotoxin will be administered as a composition at a dosage that is proportionally equivalent to a range of between 1 cc-5 cc/100 units, which translate to 100 units/cc-20 units/cc. Adjustment of these dosages depending on the greater or lesser potency of the presynaptic neurotoxins and factors identified above should be easily determined by those of ordinary skill in the art.

In one embodiment, the dosage used will be the lowest one which is still therapeutically effective (i.e., the dosage which results in detection by the patient of a reduction in the occurrence and/or magnitude of headache pain experienced by the patient, even though other symptoms associated with the pain, such as the premonitory aura, may persist). The patient's sensitivity to, and tolerance of, the presynaptic neurotoxin can be determined in the initial treatment by administering a low dosage at one site. Additional administrations of the same or different dosages can be provided as needed.

The injections will be repeated as necessary. As a general guideline, *Botulinum* toxin type A administered into or near muscle tissue has been observed to produce flaccid paralysis at target site muscles for up to about 3 to 6 months. However, increased efficacy of the treatment using *Botulinum* toxin type A is expected to happen when the toxin is administered according to the disclosed method at about 3 month intervals.

In one embodiment, commercially available BOTOX® can be reconstituted with sterile non-preserved saline prior to injection. Each vial of BOTOX® contains about 100 units of *clostridium Botulinum* toxin type A purified neurotoxin complex. Dilutions will vary depending upon the commercial preparation.

The technique of administrating presynaptic neurotoxins to modulate the parasympathetic, trigeminal and occipital nerve responses involved in TAC, migraine and other headaches associated with vascular conditions, involves distributing the presynaptic neurotoxins around the nerve endings involved. Because a high concentration of the trigeminal nerve endings are wrapped around the arteries, injections of presynaptic neurotoxins along the trajectory of the temporal extracranial artery is an effective way of administering presynaptic neurotoxins, and in particular *Botulinum* toxins, for the treatment of migraine, TAC and other headaches. The same rationale applies to the occipital nerve endings along the extracranial occipital artery. This method helps to locate the synaptic terminals of the targeted nerves, which allows for the maximum adherence of presynaptic neurotoxins to the pain generating nerves involved in headache disorders.

In one embodiment, the presynaptic neurotoxins are administered by way of injection. However, in other embodiments, the presynaptic neurotoxins may be administered topically. In general, the preparation of the presynaptic neurotoxin solution for topical delivery may be the same as that which is injected. However, in other embodiments, the presynaptic neurotoxin may be applied topically via a carrier known to those of skill in the art. The solutions can then be administered by several means, like for example, a pledget of cotton or cotton tipped applicator, a dropper or a spray in the case of a solution, or a spatula in the case of a cream. These topical methods of application may be used wherever trigeminal, occipital or parasympathetic nerve endings can be accessed efficiently by such application. The solution containing the presynaptic neurotoxins can be administered topically to the epidermis through these means and the presynaptic neurotoxins can then be distributed through the epidermis by transdermal carrier systems. As would be obvious to one of skill in the art, topical administration may not be as effective as administration via injection depending on, for example, the patient, the severity of the symptoms and access to the trigeminal, occipital and parasympathetic nerves.

The disclosed presynaptic neurotoxins can be administered with or without anesthesia or application of a topical anesthetic.

In one embodiment, the target administration sites for the current methods are the extracranial and intranasal trigeminal nerve endings and parasympathetic nerve endings of the nasal mucosa, the extracranial temporal trigeminal endings and the extracranial occipital nerve endings. The parasympathetic nerve endings in the nasal mucosa, also situated around the lacrimal glands are illustrated in FIG. 2. The trigeminal nerve endings are situated around the temporal artery (FIG. 4) and temporal muscle, as shown in FIG. 1, and the occipital nerve endings are located around the occipital arteries (FIG. 4) via cervical nerve roots that connect with the trigeminal spinal nucleus. Presynaptic neurotoxins injected in these locations every 3-6 months produce a therapeutic beneficial effect on migraine, TAC and other headaches associated with vascular conditions.

Nasal Administration

To target the intranasal trigeminal nerve endings and parasympathetic nerve endings in the nasal mucosa, the method of administration involves infiltrating the upper respiratory tract (nasal mucosa and turbinates) with a presynaptic neurotoxin diluted with a suitable solution such as saline. There is a coalescence of nerve fibers within the upper region of the nose (intranasally) near the cribriform plate and above the superior turbinate. It is also known anatomically that the inferior turbinate, which is the most responsive organ in the nose, is formed of bone and mucosa composed of vascular lakes that provide the basis for nasal sprays and topical medications administered intranasally which provide for rapid local transmucosal absorption.

In a preferred embodiment, *Botulinum* toxin Type A (BOTOX®) is used, and each nostril is infiltrated with 5 to 10 units using a solution of 100 units of BOTOX® diluted with 4 cc of normal saline. The infiltration in this preferred embodiment is performed by injection using a 30 gauge needle. Intranasal injections are given in each nostril using endoscopic application, or a needle palpation technique. The needle is inserted through the nostril. Lateral and medial mucosal infiltration is performed either through finger palpation and guidance or through direct visualization using a nasal speculum and an external light source or via endoscopic guidance.

In another embodiment, BOTOX® is used and it is administered in the region of the external nares using 5 to 10 units using a solution of 100 units of BOTOX® diluted with 4 cc of normal saline. The infiltration in this preferred embodiment is performed by injection using a 30 gauge needle. If necessary, BOTOX® can be also administered in the distribution of the infraorbital nerve.

In another embodiment, infiltration of the presynaptic neurotoxins in the upper respiratory tract will be done by topical administration to the intranasal mucosa (either alone or with a carrier substrate) which, because of its anatomical proximity to the end terminals of the trigeminal nerve or the sphenopalatine ganglion that innervate the nose, will have a direct effect on the alleviation of headache pain. In a particular embodiment, the presynaptic neurotoxin solution, with or without a carrier, will be delivered with a cotton pledget or a dropper and spread along the targeted area. In another embodiment, the presynaptic neurotoxin solution, with or without a carrier, will be delivered in the form of an emollient, cream or solution, and spread over the epidermis of the targeted area. In yet a different embodiment, the presynaptic neurotoxin solution, with or without a carrier, will be delivered in the form of a spray. Other embodiments may use alternative methods of topical delivery known to those of skill in the art.

EXAMPLE 1

A 48 yr. old female patient with chronic migraine associated with rhinorrhea and cervical dystonia was treated with the disclosed intranasal method. Her migraines involved the left hemicranium and were associated with left rhinorrhea. Initial *Botulinum* toxin treatment using migraine and cervical dystonia protocols improved her headaches, but did not completely abort them, while the rhinorrhea persisted. The patient was treated with intranasal injections of BOTOX® 2.5 units (4 cc dilution) four times on the left side only, using the needle palpation approach. There was no change in the shape of the nose or the cartilage base. The discomfort was minimal and the bleeding was not excessive. Two weeks after the treatment, both the rhinorrhea and the headache were resolved.

Temporal Administration

To target the extracranial trigeminal nerve endings in the temporal region, the extracranial temporal artery is palpated and the skin is marked where the artery's pulsations are felt. The area is then infiltrated with presynaptic neurotoxins diluted in a suitable solution such as normal saline along the course of the artery. In a preferred embodiment, the presynaptic neurotoxin used is *Botulinum* toxin type A, and the total dose given per artery is 20 units using a solution of 100 units of BOTOX® diluted with 2-4 cc of normal saline. The infiltration in this preferred embodiment is performed by injection with a 30 gauge needle.

In the case of headaches stemming from Temporal Arteritis, presynaptic neurotoxins are infiltrated around the temporal artery using a similar technique to that just described. In one embodiment, *Botulinum* toxin will be administered by injection.

In another embodiment, infiltration of the presynaptic neurotoxins along the temporal artery will be done by topical administration, in a similar way as that described for the intranasal area. In a particular embodiment, the presynaptic neurotoxin solution will contain a transdermal carrier. In a different embodiment, the presynaptic neurotoxin solution will be delivered in the form of a spray along the temporal artery, and care will be taken to shield the non-targeted areas of the scalp.

Occipital Administration

The occipital artery can be treated in a similar fashion. The artery is located using the following landmarks: the midpoint between the nuchal ridge (inion) and the mastoid process is found; light palpation is used to feel the occipital artery's pulse. The hair is separated and the skin is marked along the course of the artery. Presynaptic neurotoxins diluted in normal saline or other suitable solution are infiltrated around each artery. In a preferred embodiment, 20 units of BOTOX® in divided doses are infiltrated around each artery using a solution of 100 units of BOTOX® diluted with 2-4 cc of normal saline. The infiltration in this preferred embodiment is performed by injection with a 30 gauge needle.

In another embodiment, infiltration of the presynaptic neurotoxins along the occipital artery will be done by topical administration, in the same way described earlier for the temporal administration.

Depending on the condition of each patient, the presynaptic neurotoxins will be administered to one of the sites just described, or to multiple sites. In one embodiment, there are multiple administration sites. In a particular preferred embodiment, the doses ranging between 25 units and 250 units are equally divided among the different administration sites. One of skill in the art should readily ascertain how to adjust the number of administration sites and dosages based on individual profiles of weight, gender, age, condition severity and symptoms.

Administration to the Sphenopalatine Ganglion

In one embodiment, a direct sphenopalatine administration of presynaptic neurotoxins can be used, which in a preferred embodiment will be *Botulinum* toxins, and in particular, *Botulinum* toxin type A. In another embodiment, this treatment may follow prior treatments in which the presynaptic neurotoxin had been administered at any of the foregoing sites without sufficient results. In another embodiment, this treatment is the sole treatment administered to the patient, Migraine and TAC involve increased activity of the trigeminal nerve and its brainstem nucleus, the trigeminal nucleus caudalis (TNC). Interneurons connect the TNC to the solitary nucleus in the brainstem. The solitary nucleus projects to the sphenopalatine ganglion which supplies intracranial blood vessels and the nasal mucosa. Increased activity in the sphenopalatine ganglion leads to dilation of blood vessels which may contribute to the throbbing component of the headache and may also be responsible for the nasal symptoms associated with migraine.

The sphenopalatine ganglion, the largest of the sympathetic ganglion associated with the braches of the trigeminal nerve, is deeply placed in the ptergopalatine fossa, close to the sphenopalatine foramen. It is triangular or heart shaped, of a reddish-gray color, and is situated just below the maxillary nerve as it crosses the fossa. It receives a sensory, a motor and a sympathetic root. The sensory root is derived from two sphenopalatine branches of the maxillary nerve; their fibers, for the most part, pass directly into the palatine nerves. A few of the fibers, however, enter the ganglion, constituting its sensory root. The motor root is derived from the nervus intermedius through the greater superficial petrosal nerve and consists, in part, of sympathetic efferent (preganglionic) fibers from the medulla. In the sphenopalatine ganglion, they form synapses with neurons whose postganglionic axons, vasodilator and secretory fibers, are distributed with the deep branches of the trigeminal to the mucous membrane of the nose, soft palate, tonsils, uvula, roof of the mouth, upper lip and gums, and to the upper part of the pharynx. The sympathetic root is derived from the carotid plexus through the deep petrosal nerve. These two nerves join to form the nerve of the pterygoid canal before their entrance into the ganglion.

*Botulinum* toxins generally bind to nerve endings close to their synapses, but may penetrate unmyelinated nerves, and even ganglia, if delivered at high dose in close proximity to these structures. Sphenopalatine nerve blocks have been used to treat migraines by inserting nasal swabs soaked in a local anesthetic into the posterior nares and allowed to diffuse to the sphenopalatine ganglion.

The present disclosure provides alternative methods for delivery of presynaptic neurotoxins to the sphenopalatine ganglion comprising injection of the neurotoxins into the vicinity of the sphenopalatine ganglion as depicted in FIGS. 5-8.

In one embodiment, a patient in need of treatment for a headache disorder is examined by careful palpation of the skull. The anterior temporal fossa 102 is identified at a position halfway between the tragus of the ear 104 and the outer cantus of the eye 106. The injection site 108 is identified (FIG. 5) at the anterior temporal fossa 102.

In one instance, a syringe 110 containing a concentrated solution of the presynaptic neurotoxin, such as a *botulinum* toxin type A, and 1.5 inch 27 gauge needle 112 are used to prevent substantial diffusion of the neurotoxin from the treatment site. A concentrated solution of *botulinum* toxin is preferably used, such as, for example and in the case of utilizing BOTOX® (*botulinum* toxin type A), 1 cc of normal unpreserved saline per 100 unit vial of BOTOX®. In additional embodiments, from about 2 cc to 4 cc dilutions per 100 units of BOTOX® are suitable.

In various administration methods, needles of various sizes can be utilized, such as, for example, about 1.5 to about 2 inches long and of 30, 27 or even 25 gauge can be used. Preferably, the needle selected is at least about 1 inch long.

Figure 7:
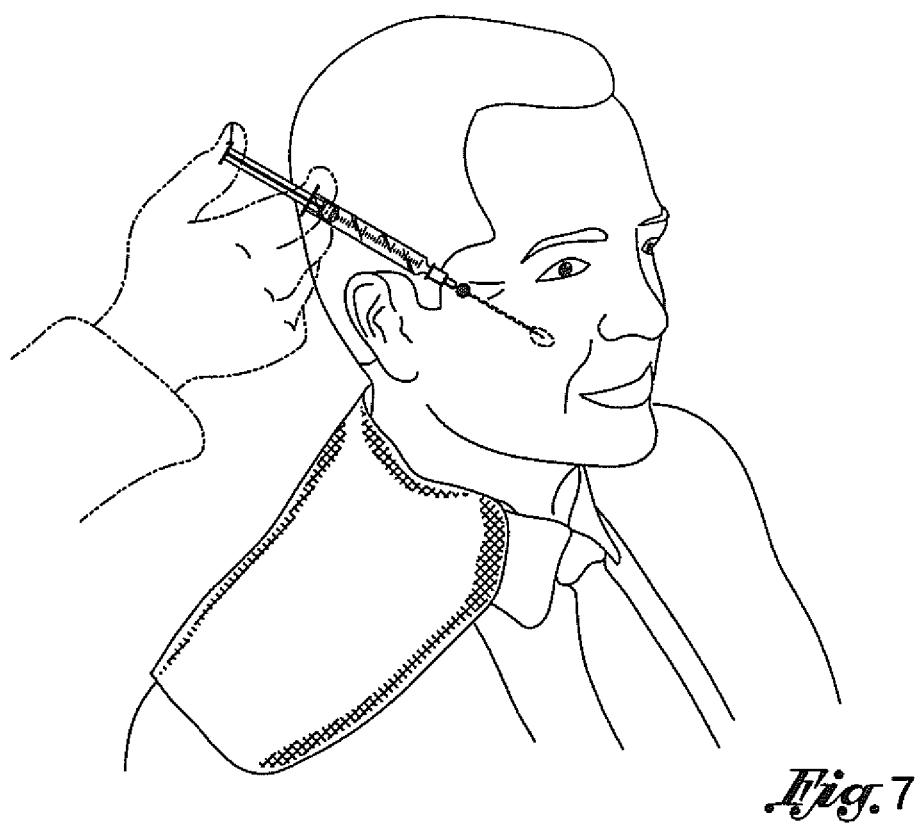
FIG. 7 depicts one embodiment of the disclosed method wherein discontinuous discreet injections of postsynaptic neurotoxin are administered to or around the sphenopalatine ganglion.
Figure 8:
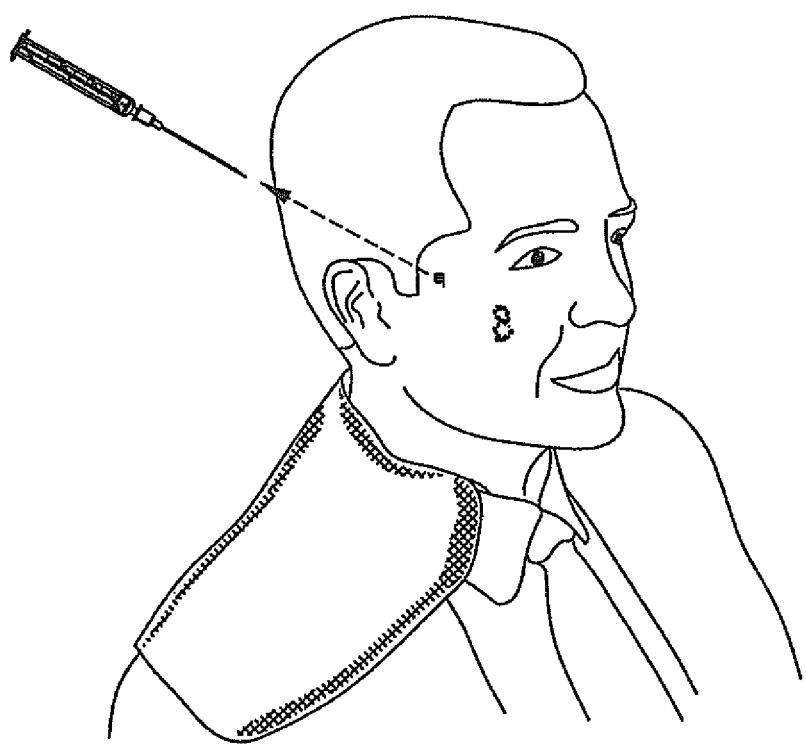
FIG. 8 depicts the withdrawal of the needle along an injection track.

The needle is inserted at injection site 108 through the subcutaneous tissue, through the temporalis muscle, angling forwards at an angle α. Angle α is in the range of about 50-70 degrees relative to a vertical plane alongside the head of the patient, substantially parallel to the sagittal plane, such that the needle's entry path is behind the zygomatic arch. The needle does not penetrate the periosteum. The needle is preferably inserted to its full length (although not necessarily, as dependant upon needle length and patient anatomy, of course), until the maxillary bone is reached and the syringe is moved forward (to move the needle dorsally). The angle of this forward movement is in the range of about 10-40 degrees. The needle is then slowly retracted to position 114 at which time injection of presynaptic neurotoxin is administered (FIGS. 7 and 8). In one embodiment of the disclosed methods, the toxin solution is injected in the area of the sphenopalatine ganglion (FIG. 7). Upon injection of the desired volume of presynaptic neurotoxin, the needle is withdrawn (FIG. 8). While the sphenopalatine ganglion is described herein, administration to other ganglion in order to interfere with impulse transmission, as described herein, is also contemplated.

The injections can administered unilaterally or bilaterally, based upon the location of the headache.

EXAMPLE 2

A female patient presents with chronic migraines. Her migraines involved the right hemicranium. The patient is treated with a sphenopalatine ganglion targeted injection of BOTOX® of about 100 units (in a 1 cc dilution) in a continuous injection method on the right side only, using the disclosed technique, to distribute the toxin around the sphenopalatine ganglion (thus minimizing/avoiding administration of toxin to the temporalis muscle). The discomfort is minimal and the bleeding is not excessive. The patient remains upright (e.g. substantially vertical) after toxin administration (from about 15 min to 3 hours, more preferably from about 1 to about 3 hours and most preferably from about 2 to about 3 hours), to allow toxin to remain concentrated at the sphenopalatine ganglion and not be distributed throughout the temporalis muscle. Two weeks after the treatment, the headache is resolved.

EXAMPLE 3

A male patient presents with bilateral cluster headaches. The patient is treated with bilateral sphenopalatine ganglion injections of BOTOX® (*botulinum* toxin type A at 50 units per side, (in a 1 cc dilution, i.e. 50 units per/cc/side) at a plurality of sites along the injection needle track, around the sphenopalatine ganglion (thus minimizing/avoiding administration of toxin to the temporalis muscle). The discomfort is minimal and the bleeding is not excessive. The patient remains upright (e.g. substantially vertical) after toxin administration (from about 15 min to 3 hours, more preferably from about 1 to about 3 hours and most preferably from about 2 to about 3 hours), to allow toxin to remain concentrated at the sphenopalatine ganglion and not be distributed through out the temporalis muscle, as above. Two weeks after the treatment, the headache is resolved.

EXAMPLE 4

A female patient presents with rhinorrhea. The patient is treated with unilateral or bilateral sphenopalatine ganglion injections of BOTOX® (*botulinum* toxin type A at 50 units per side, (in a 1 cc dilution, i.e. 50 units per/cc/side) at a plurality of sites along the injection needle track, around the sphenopalatine ganglion (thus minimizing/avoiding administration of toxin to the temporalis muscle). The discomfort is minimal and the bleeding is not excessive. The patient remains upright (e.g. substantially vertical) after toxin administration (from about 15 min to 3 hours, more preferably from about 1 to about 3 hours and most preferably from about 2 to about 3 hours), to allow toxin to remain concentrated at the sphenopalatine ganglion and not be distributed through out the temporalis muscle, as above. The rhinorrhea is resolved in 24 to 72 hours.

EXAMPLE 5

A male, age 65, with excessive lacrimation is treated with unilateral or bilateral sphenopalatine ganglion injections of BOTOX® (*botulinum* toxin type A at 50 units per side (in a 1 cc dilution, i.e. 50 units per/cc/side) at a plurality of sites along the injection needle track, around the sphenopalatine ganglion (thus minimizing/avoiding administration of toxin to the temporalis muscle). The discomfort is minimal and the bleeding is not excessive. The patient remains upright (e.g. substantially vertical) after toxin administration (from about 15 min to 3 hours, more preferably from about 1 to about 3 hours and most preferably from about 2 to about 3 hours), to allow toxin to remain concentrated at the sphenopalatine ganglion and not be distributed through out the temporalis muscle, as above. All symptoms would be reduced or eliminated with toxin therapy in about 1-7 days. Duration would be weeks to several months.

Other Administration Sites

In the case of atherosclerotic disease, presynaptic neurotoxins, preferably *Botulinum* toxins can be injected directly into the plaque via an intra-arterial catheter. *Botulinum* toxins will be of benefit as these plaques produce inflammation in the blood vessel wall in response to cholesterol deposits. This inflammation further compromises the diameter of the lumen of the blood vessel. *Botulinum* toxins will focally reduce this inflammation for 3 to 6 months.

For the administration of presynaptic neurotoxins by injection, dilution dependent syringes with gauging for units rather than volume injected are recommended. This will ensure that the volume injected contains the desired amount of units, since the volume injected will depend on how the original concentration of the presynaptic neurotoxin was diluted when reconstituted. For example, in the embodiment in which 100 units of *Botulinum* toxin type A are reconstituted in 4 cc of normal saline, a specific syringe with demarcations at 0.1 cc of 2.5 units, and at 0.2 cc of 5 units will be used. In another embodiment in which 100 units of *Botulinum* toxin type A are reconstituted in 1 cc of normal saline, the syringe with demarcations at 0.1 cc of 10 units; and at 0.2 cc of 20 units will be used. These delivery tools allow for accurate delivery and recording of the dose given.

The invention having been fully described, examples illustrating its practice should not, however, be considered to limit the scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A method for reduction of pain associated with a headache in a mammal in need thereof, comprising the step of administering a therapeutically effective amount of a *botulinum* toxin selected from the group consisting of *botulinum* toxin type A, B, $C_1$, D, E and F along the trajectory of an extracranial artery and to a sphenopalatine ganglion, wherein the extracranial artery is selected from the group consisting of a temporal artery and an occipital artery, thereby effecting reduction of headache pain in the mammal in need thereof.

2. The method of claim 1, wherein the *botulinum* toxin is administered by injection.

3. The method of claim 1, wherein the *botulinum* toxin is *botulinum* toxin type B.

4. The method of claim 1, wherein the headache is selected from the group consisting of migraine, trigeminal autonomic cephalgia and headache caused by a vascular condition.

5. The method of claim 1, further comprising the step of locating the extracranial artery.

6. The method of claim 5, wherein the step of locating the extracranial artery utilizes palpation.

7. The method of claim 1, wherein administration to the sphenopalatine is performed bilaterally.

8. The method of claim 1, wherein administration of *botulinum* toxin is to a plurality of locations adjacent the sphenopalatine ganglion.

9. A method for reduction of a pain associated with a headache in a mammal in need thereof, the method comprising the steps of; determining the projection of an extracranial artery wherein the extracranial artery is selected from the group consisting of a temporal artery and an occipital artery; infiltrating an area around the extracranial artery with a therapeutically effective amount of a *botulinum* toxin selected from the group consisting *botulinum* toxin type A, B, $C_1$, D, E, F and G; administering *botulinum* toxin to a sphenopalatine ganglion, thereby reducing the pain associated with the headache.

10. The method of claim 9, wherein the determining step utilizes palpation to determine the projection of the extracranial artery.

11. The method of claim 9, wherein the step of infiltrating the area around the extracranial artery utilizes injection or topical administration of *botulinum* toxin.

12. The method of claim 9, wherein the step of administering *botulinum* toxin to the sphenopalatine ganglion utilizes injection or topical administration of *botulinum* toxin.

13. The method of claim 9 wherein the infiltrating and administering steps are performed unilaterally or bilaterally.

14. The method of claim 9, wherein the headache is selected from the group consisting of migraine, trigeminal autonomic cephalgia and headache caused by a vascular condition.

15. A method of reducing pain, wherein the pain is associated with a headache, in a mammal in need thereof, comprising: a first administering step wherein a therapeutically effective amount of a *botulinum* toxin selected from the group consisting of *botulinum* toxin type A, B, $C_1$, D, E, F and G is administered along the trajectory of an extracranial artery wherein the extracranial artery is selected from the group consisting of a temporal artery and an occipital artery; and a second administering step, wherein a therapeutically effective amount of *botulinum* toxin is administered to a sphenopalatine ganglion, wherein the second administration step is provided when prior treatment targeted to the extracranial artery do not provide sufficient results, thereby reducing the pain associated with the headache.

16. The method of claim 15, wherein the second administration step of *botulinum* toxin to the sphenopalatine ganglion is via an injection site.

17. The method of claim 15, wherein the injection site is midway between the tragus of the ear and outer cantus of the eye.

18. The method of claim 15, wherein the *botulinum* toxin is *botulinum* toxin type B.

* * * * *